United States Patent
Cleary et al.

(10) Patent No.: US 8,232,412 B2
(45) Date of Patent: Jul. 31, 2012

(54) DIAZONIUM-FREE METHOD TO MAKE AN INDAZOLE INTERMEDIATE IN THE SYNTHESIS OF BICYCLIC 5-(TRIFLUORMETHOXY)-1H-3-INDAZOLECARBOXYLIC ACID AMIDES

(75) Inventors: Thomas Cleary, Florence, SC (US); Yaohui Ji, Shanghai (CN); Thimma Rawalpally, Florence, SC (US)

(73) Assignee: Hoffmann-La Roche Inc., Nutley, NJ (US)

( * ) Notice: Subject to any disclaimer, the term of this patent is extended or adjusted under 35 U.S.C. 154(b) by 448 days.

(21) Appl. No.: 12/576,259

(22) Filed: Oct. 9, 2009

(65) Prior Publication Data

US 2010/0094011 A1    Apr. 15, 2010

Related U.S. Application Data

(60) Provisional application No. 61/104,777, filed on Oct. 13, 2008.

(51) Int. Cl.
*C07D 231/56* (2006.01)
*C07D 231/54* (2006.01)

(52) U.S. Cl. .................. 548/362.5; 548/361.1

(58) Field of Classification Search ............. 548/362.5, 548/361.1
See application file for complete search history.

(56) References Cited

FOREIGN PATENT DOCUMENTS

| DE | 102004054666 | 5/2006 |
|----|---|---|
| WO | WO 2005/063767 | 7/2005 |
| WO | WO 2005/092890 | 10/2005 |
| WO | WO 2005/111038 | 11/2005 |
| WO | WO 2006/001894 | 1/2006 |
| WO | WO 2006/063841 | 6/2006 |
| WO | WO 2006/069097 | 6/2006 |

OTHER PUBLICATIONS

Ansel, et al., Pharm. Dosage Forms & Drug Delivery Systems (1995) pp. 456-457.
Zhang, et al., Bioorg. Med. Chem. Lett. vol. 9, 1999, pp. 319-321.
Elliott E. et al, "Total Syntehesis of Nigllicine and Nigeglanine Hydrobromide" Organic Letters,7:12 2449-2451 (2005) XP00256430.
Stolle R. and Becker W., "Uber N-Amino-isatin" Chemische Berichte, 57: (1924) 1123-1124 XP002564631.

*Primary Examiner* — Charanjit Aulakh
(74) *Attorney, Agent, or Firm* — George W. Johnston; Patricia S. Rocha-Tramaloni; Kimberly J. Prior

(57) ABSTRACT

The present invention provides novel methods for preparing 5-(trifluoromethoxy)-1H-3-indazolecarboxylic acid (3), which is a useful precursor for the preparation of bicyclic-5-trifluoromethoxy-1H-indazole-3-carboxylic acid amides of Formula (1). Compounds of Formula (1) are active as agonists and partial agonists of the nicotinic α-7 receptor and are being studied for their use in the treatment of disease conditions associated with defective or malfunctioning nicotinic acetylcholine receptors, especially of the brain, such as for the treatment of Alzheimer's disease and schizophrenia, as well as other psychiatric and neurological disorders. The present methods are useful for preparing compound (3) on scale up levels.

9 Claims, No Drawings

DIAZONIUM-FREE METHOD TO MAKE AN INDAZOLE INTERMEDIATE IN THE SYNTHESIS OF BICYCLIC 5-(TRIFLUORMETHOXY)-1H-3-INDAZOLECARBOXYLIC ACID AMIDES

PRIORITY TO RELATED APPLICATIONS

This application claims the benefit of U.S. Provisional Application No. 61/104,777, filed Oct. 13, 2008, which is hereby incorporated by reference in its entirety.

FIELD OF THE INVENTION

The present invention provides novel methods for preparing 5-(trifluoromethoxy)-1H-3-indazolecarboxylic acid (3), a useful precursor for the preparation of various bicyclic amides of Formula (1), which are active as agonists and partial agonists of the nicotinic α-7 receptor. Compounds of Formula (1) are being studied for their use in the treatment of disease conditions associated with defective or malfunctioning nicotinic acetylcholine receptors, especially of the brain, such as for the treatment of Alzheimer's disease and schizophrenia, as well as other psychiatric and neurological disorders. The present methods are useful for preparing compound (3) on scale up levels.

BACKGROUND OF THE INVENTION

Bicyclic indazole amides of Formula (1) are described in WO 2005/063767, WO 2005/092890, WO 2005/111038, WO 2006/001894 and WO 2006/069097

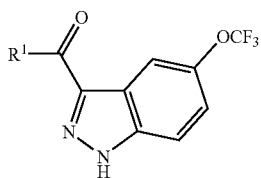

(1)

wherein
$R^1$ is

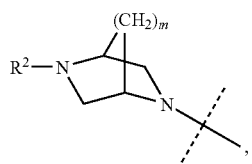

wherein
$R^2$ is H, or $C_{1-4}$-alkyl (e.g., $CH_3$) which is unsubstituted or substituted one or more by F, Cl, Br, I, CN, OH, alkoxy having 1 to 4 carbon atoms (e.g., $OCH_3$), $NR^4R^5$, or combinations thereof;
$R^4$ and $R^5$ are each independently H or Ar, Ar—$C_{1-4}$-alkyl, Het, $C_{1-4}$-alkyl (e.g., $CH_3$), $C_{3-8}$-cycloalkyl (e.g., cyclopropyl), or $C_{4-8}$-cycloalkylalkyl (e.g., cyclopropylmethyl), each of which is unsubstituted or substituted one or more times by F, Cl, Br, I, CN, OH, alkoxy having 1 to 4 carbon atoms (e.g., $OCH_3$), monoalkylamino, dialkylamino (e.g., diethylamino), $C_{3-8}$-cycloalkyl, or combinations thereof,
and
m is 1, 2 or 3;
or
$R^1$ is $A_1$, wherein $A_1$ is

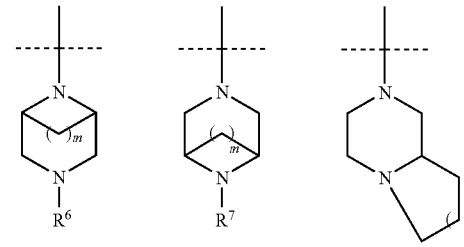

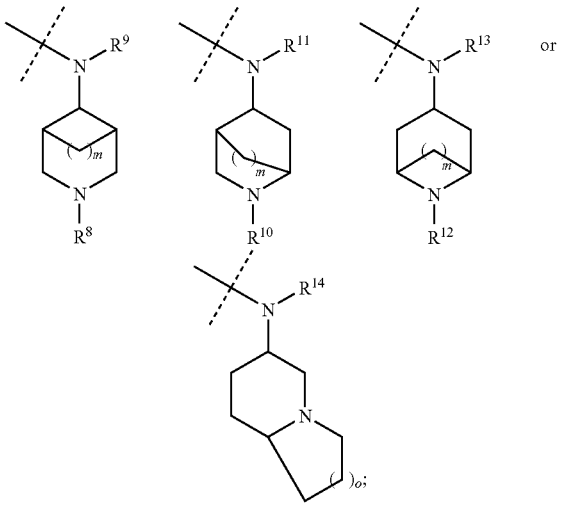

wherein $R^6$ to $R^{14}$ are each, independently,
H,
$C_{1-4}$-alkyl (e.g., $CH_3$) which is unsubstituted or substituted one or more times by F, Cl, Br, I, CN, alkoxy having 1 to 4 carbon atoms (e.g., $OCH_3$), Ar (e.g., phenyl) or combinations thereof,
$C_{3-6}$-alkenyl which is unsubstituted or substituted one or more times by F, Cl, Br, I, CN, alkoxy having 1 to 4 carbon atoms (e.g., $OCH_3$), Ar (e.g., phenyl) or combinations thereof,
$C_{3-6}$-alkynyl which is unsubstituted or substituted one or more times by F, Cl, Br, I, CN, alkoxy having 1 to 4 carbon atoms (e.g., $OCH_3$), or Ar (e.g., phenyl) or combinations thereof,
cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl),
cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy or combinations thereof (e.g., cyclopentylmethyl, cyclopropylmethyl, etc.),
Ar-alkyl (e.g., benzyl), or
Het-alkyl (e.g., thienylmethyl);

wherein

Ar
is an aryl group containing 6 to 10 carbon atoms which is unsubstituted or substituted one or more times by
alkyl having 1 to 8 carbon atoms,
alkoxy having 1 to 8 carbon atoms,
halogen (F, Cl, Br, or I, preferably F or Cl),
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkylaminocarbonyl,
acylamido (e.g., acetamido),
acyloxy (e.g., acetoxy),
alkylthio having 1 to 8 carbon atoms,
alkylsulphinyl having 1 to 8 carbon atoms,
alkylsulphonyl having 1 to 8 carbon atoms,
sulfo,
sulfonylamino,
Het,
cycloalkylamino wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio,
aryloxy wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio,
arylthio wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio,
cycloalkyloxy wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio, or
combinations thereof;

Ar-alkyl
is an aryl-alkylene group (e.g., benzyl, phenethyl, phenpropyl) wherein the alkylene portion contains 1 to 4 carbon atoms and is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio, and the aryl portion is Ar as defined above; and Het
is a heterocyclic group, which is fully saturated, partially saturated or fully unsaturated, having 5 to 10 ring atoms in which at least 1 ring atom is a N, O or S atom, which is unsubstituted or substituted one or more times by
alkyl having 1 to 8 carbon atoms,
alkoxy having 1 to 8 carbon atoms,
halogen (F, Cl, Br, or I, preferably F or Cl),
amino,
cyano,
hydroxyl,
nitro,
halogenated alkyl having 1 to 8 carbon atoms,
halogenated alkoxy having 1 to 8 carbon atoms,
hydroxyalkyl having 1 to 8 carbon atoms,
hydroxyalkoxy having 2 to 8 carbon atoms,
alkenyloxy having 3 to 8 carbon atoms,
monoalkylamino having 1 to 8 carbon atoms,
dialkylamino wherein the alkyl portions each have 1 to 8 carbon atoms,
carboxy,
alkoxycarbonyl,
alkoxycarbonylmethyl,
alkylaminocarbonyl,
acylamido (e.g., acetamido),
acyloxy (e.g., acetoxy),
alkylthio having 1 to 8 carbon atoms,
alkylsulphinyl having 1 to 8 carbon atoms,
alkylsulphonyl having 1 to 8 carbon atoms,
oxo,
sulfo,
sulfonylamino,
cycloalkylamino wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio,
aryl containing 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio, aryl-alkylene group (e.g., benzyl, phenethyl, phenpropyl) wherein the aryl portion contains 6 to 10 carbon atoms and the alkylene portion contains 1 to 4 carbon atoms and is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio, aryloxy wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 C atoms, dialkylamino wherein the alkyl portions each have 1 to 8 carbon atoms, $COR^{17}$, $CSR^{17}$, cyano, hydroxyl, nitro, oxo, or thio, arylthio wherein the aryl portion contains 6 to 10 carbon atoms (e.g., phenyl, naphthyl, biphenyl) and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio, cycloalkyloxy wherein the cycloalkyl group has 3 to 7 carbon atoms and is optionally substituted by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio, heterocyclic group, which is fully saturated, partially saturated or fully unsaturated, having 5 to 10 ring atoms in which at least 1 ring atom is a N, O or S atom, which is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio (e.g., furyl, thienyl, methylthienyl, bithienyl, benzylprazolyl, thiazolyl, imidazolyl, methylimidazolyl, pyrrolidinyl, morpholinyl, thiomorpholinyl), heterocyclic-alkyl group, in which the heterocyclic portion is fully saturated, partially saturated or fully unsaturated, having 5 to 10 ring atoms in which at least 1 ring atom is a N, O or S atom, and the alkyl portion is an alkylene group containing 1-4 carbon atoms, wherein said heterocyclic-alkyl group is unsubstituted or substituted one or more times by halogen (F, Cl, Br, or I, preferably F or Cl), alkyl having 1 to 8 carbon atoms, halogenated alkyl having 1 to 8 carbon atoms, alkoxy having 1 to 4 carbon atoms, amino, monoalkylamino wherein the alkyl portion has 1 to 8 carbon atoms, dialkylamino wherein the alkyl portions each have 1 to 8 carbon atoms, $COR^{17}$, $CSR^{17}$, cyano, hydroxyl, nitro, oxo, or thio (e.g., piperidinylethyl), or combinations thereof;

$R^{15}$ and $R^{16}$ are each independently

H,

Ar,

Ar-alkyl (e.g., benzyl, fluorobenzyl, methoxybenzyl, phenethyl, phenpropyl),

Het, $C_{1-4}$-alkyl (e.g., $CH_3$) which is unsubstituted or substituted one or more times by F, Cl, Br, I, CN, OH, alkoxy having 1 to 4 carbon atoms (e.g., $OCH_3$), monoalkylamino, dialkylamino (e.g., diethylamino), $C_{3-8}$-cycloalkyl, or combinations thereof, cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl), $C_{3-6}$-alkenyl which is unsubstituted or substituted one or more times by F, Cl, Br, I, CN, alkoxy having 1 to 4 carbon atoms (e.g., $OCH_3$), Ar (e.g., phenyl) or combinations thereof, or $C_{3-6}$-alkynyl which is unsubstituted or substituted one or more by F, Cl, Br, I, CN, alkoxy having 1 to 4 carbon atoms (e.g., $OCH_3$), or Ar (e.g., phenyl) or combinations thereof;

$R^{17}$ is H, $C_{1-6}$-alkyl (e.g., $CH_3$) which is unsubstituted or substituted one or more times by F, Cl, Br, I, CN, OH, alkoxy having 1 to 4 carbon atoms (e.g., $OCH_3$), $NR^{15}R^{16}$, SH, $SR^{15}$, $SOR^{16}$, $C_{3-8}$-cycloalkyl, $SO_2R^{15}$, $SO_2NR^{15}R^{16}$, Ar, Het, or combinations thereof, $C_{3-6}$-alkenyl which is unsubstituted or substituted one or more by F, Cl, Br, I, CN, OH, alkoxy having 1 to 4 carbon atoms (e.g., $OCH_3$), $NR^{15}R^{16}$, SH, $SR^{15}$, $SOR^{15}$, $C_{3-8}$-cycloalkyl, $SO_2R^{15}$, $SO_2NR^{15}R^{16}$, Ar, Het, or combinations thereof, $C_{3-6}$-alkynyl which is unsubstituted or substituted one or more by F, Cl, Br, I, CN, OH, alkoxy having 1 to 4 carbon atoms (e.g., $OCH_3$), $NR^{15}R^{16}$, SH, $SR^{15}$, $SOR^{15}$, $C_{3-8}$-cycloalkyl, $SO_2R^{15}$, $SO_2NR^{15}R^{16}$, Ar, Het, or combinations thereof, $C_{3-8}$-cycloalkyl which is unsubstituted or substituted one or more times by F, Cl, Br, I, CN, OH, alkoxy having 1 to 4 carbon atoms (e.g., $OCH_3$), $NR^{15}R^{16}$, SH, $SR^{15}$, $SOR^{15}$, unsubstituted $C_{3-8}$-cycloalkyl, $SO_2R^{15}$, $SO_2NR^{15}R^{16}$, Ar, Het, or combinations thereof, $C_{4-8}$-cycloalkylalkyl which is unsubstituted or substituted one or more times by F, Cl, Br, I, CN, OH, alkoxy having 1 to 4 carbon atoms (e.g., $OCH_3$), $NR^{15}R^{16}$, SH, $SR^{15}$, $SOR^{15}$, unsubstituted $C_{3-8}$-cycloalkyl, $SO_2R^{15}$, $SO_2NR^{15}R^{16}$, Ar, Het, or combinations thereof, m is as described above;

and o is 1 or 2;

or

R¹ is

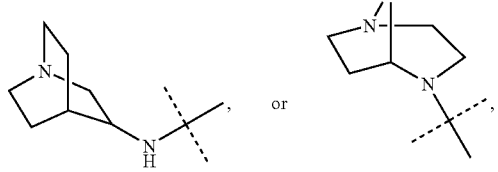

wherein m is as described above.

The compounds of Formula (1), described in WO 2005/063767, WO 2005/092890, WO 2005/111038, WO 2006/001894 and WO 2006/069097, are being studied to determine their potential as oral agents as a nicotinic α-7 receptor partial agonists, acting on a highly specialized receptor found in the central nervous system. Compounds that act on this receptor could be beneficial in the treatment of Alzheimer's disease and schizophrenia, as well as other psychiatric and neurological disorders.

Methods for the preparation of (1) are also set out in WO 2005/063767, WO 2005/092890, WO 2005/111038, WO 2006/001894 and WO 2006/069097, which disclose that compounds of Formula (1) can be prepared from the appropriate bicyclobase R¹H, wherein R¹ is as described above, and 5-(trifluoromethoxy)-1H-3-indazolecarboxylic acid (3), as shown below in Scheme 1.

Scheme 1

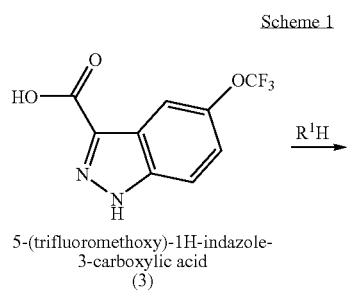

5-(trifluoromethoxy)-1H-indazole-
3-carboxylic acid
(3)

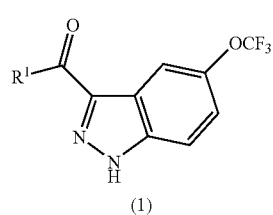

(1)

Compound (3) is a key intermediate for the synthesis of compounds of Formula (1). A synthetic route for intermediate (3) is disclosed in WO 2005/063767, WO 2005/092890, WO 2005/111038, WO 2006/001894 and WO 2006/069097. This synthetic route involves a diazotization reaction of 5-trifluoromethoxyisatin in moderate yield. However, such aromatic diazonium salts (5) are not generally stable at temperatures above 5° C. (Richard C. Wedlich, Chemical Engineering Progress, October 2001), which makes them less suitable for large-scale preparations.

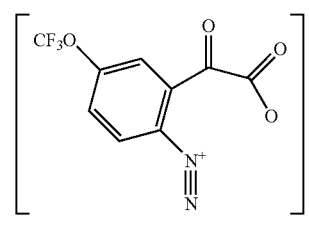

Diazonium intermediate

Accordingly, novel, efficient methods for preparing (3) are sought.

SUMMARY OF THE INVENTION

The present invention provides a method for preparing compound (3) having the formula:

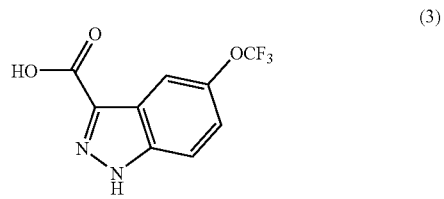

which comprises:

(a) reacting 5-trifluoromethoxyisatin with a ketone-protecting reagent in a solvent to provide a ketone-protected compound;

(b) treating the ketone-protected compound from step (a) with an electrophilic aminating reagent in an inert solvent to provide an electrophilically aminated compound; and (c) hydrolyzing the electrophilically aminated compound from step (b) under basic conditions to form a ring opened intermediate and treating the intermediate with aqueous acid to ring close the intermediate and remove the ketone-protecting reagent to provide (3).

DETAILED DESCRIPTION OF THE INVENTION

As used herein, the following terms have the meanings set out below.

The term "inert organic solvent" refers to a solvent that does not interfere chemically with the reaction.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hydroscopicity, and solubility of compounds. See, e.g., H. Ansel et. al., Pharmaceutical Dosage Forms and Drug Delivery Systems (6$^{th}$ Ed. 1995) at pp. 196 and 1456-1457.

The term "prodrug" refers to compounds, which undergo transformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The present invention provides novel methods for preparing key intermediate 5-(trifluoromethoxy)-1H-3-indazolecarboxylic acid (3) via a diazonium free route that is safe and easily scalable. The novel methods provide (3) in three steps starting from commercially available 5-trifluoromethoxyisatin (4) set out in Scheme 2 below.

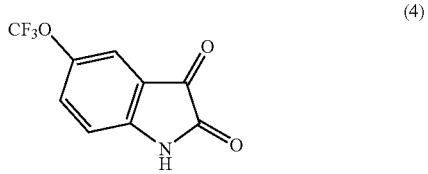

(4)

The reactive ketone functionality in (4) can be protected with a ketone-protecting reagent in a solvent to form a ketone-protected compound. Any ketone-protecting reagent that does not interfere with subsequent reactions in the present invention may be employed. Protection of ketones with ketone-protecting reagents is well known and is discussed, for example, in Greene's Protective Groups in Organic Synthesis, 4th Edition, J. F. Wuts et al., Wiley InterScience, 2006, Chapter 4. Illustrative non-limiting examples of ketone-protected compounds include dialkyl ketals and cyclic ketals. Dialkyl ketals include dimethoxy ketals, diethoxy ketals, mixed dialkyl ketals, and the like. Cyclic ketals include 1,3 dioxolan ketals, and the like.

Preferably, the ketone-protecting reagent is HC(OEt)$_3$/EtOH and the preferred ketone-protected compound is diethoxy ketal (diethyl acetal), 3,3-diethoxy-5-trifluoromethoxyisatin (7) set out in Scheme 2 below. Preferably, the ketone-protected compound is prepared by heating to reflux a mixture of (7), a strong acid cation exchange resin such as Amberlite® FPC22H resin, HC(OEt)$_3$, and absolute ethanol.

The ketone-protected compound can then be treated with an electrophilic aminating reagent in an inert solvent to provide an electrophilically aminated compound. Any electrophilic aminating reagent that does not interfere with subsequent reactions in the present invention may be employed. Electrophilic amination of amines with electrophilic aminating reagents is well known. Illustrative non-limiting examples of electrophilic aminating reagents include amino-, alkyl amino- and acylamino-groups. Preferred electrophilic aminating agents are chloramine, hydroxylamine-O-sulphonic acid, oxaziridines unsubstituted at the nitrogen atom, and N-acyloxaziridines, and the like.

Preferably, the electrophilic aminating reagent is 4-nitrobenzoyl O-hydroxylamine and the electrophilically aminated compound is N-amino-3,3-diethoxy-5-trifluoromethoxyisatin (6) set out in Scheme 2 below. Preferably, the electrophilic aminated compound is prepared by sequentially admixing (7) and N-methylpyrrolidone, adding to the mixture potassium tert-butoxide solution in tetrahydrofuran at <25° C., and then adding to the mixture 4-nitrobenzoyl O-hydroxylamine in N-methylpyrrolidone.

In a one-pot reaction, the electrophilic aminated compound can then be hydrolyzed under basic conditions to form a ring opened intermediate and the intermediate can then be treated with aqueous acid to ring close the intermediate and remove the ketone-protecting reagent to provide (3) as set out below in Scheme 2. Preferably, the hydrolysis is carried out under basic conditions with aqueous sodium hydroxide and the intermediate is treated with aqueous acetic acid at <5° C.

Scheme 2

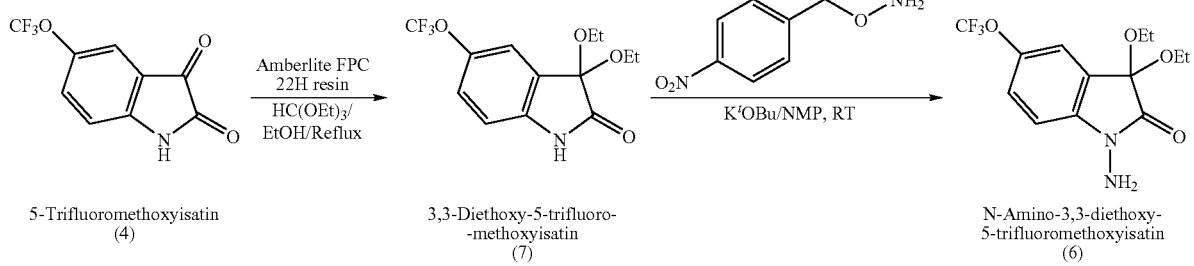

5-Trifluoromethoxyisatin
(4)

3,3-Diethoxy-5-trifluoro--methoxyisatin
(7)

N-Amino-3,3-diethoxy-5-trifluoromethoxyisatin
(6)

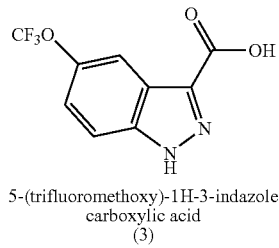

5-(trifluoromethoxy)-1H-3-indazole carboxylic acid (3)

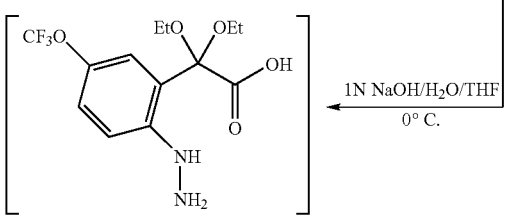

In a preferred embodiment, compound (6) can be prepared in two steps starting from commercially available (4) as set out below. First, intermediate (7) can be prepared by heating to reflux (4) with triethyl orthoformate in ethanol in the presence of a strong acidic resin.

The final reaction is the one-pot base-catalyzed ring opening of (6) using 1N aqueous sodium hydroxide in tetrahydrofuran (THF) followed by removal of the diethyl acetal group and cyclization of the intermediate with 2M acetic acid to provide (3) in excellent yield and purity.

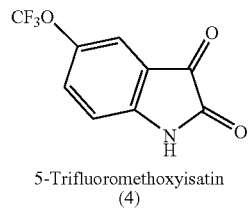

5-Trifluoromethoxyisatin (4)

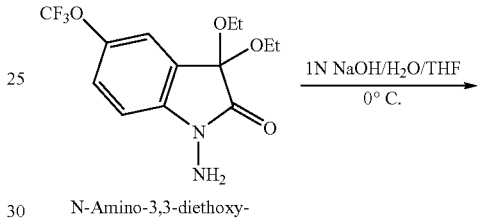

N-Amino-3,3-diethoxy-5-trifluoromethoxyisatin (6)

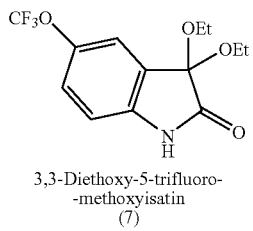

3,3-Diethoxy-5-trifluoro-methoxyisatin (7)

Electrophilic amination of (7) using a O-benzoyl hydroxylamine derivative in the presence of potassium-t-butoxide at 20° C. in N-methylpyrrolidone (NMP) yields (6).

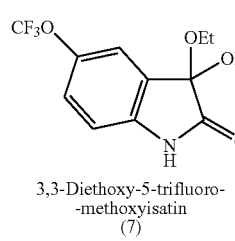

3,3-Diethoxy-5-trifluoro-methoxyisatin (7)

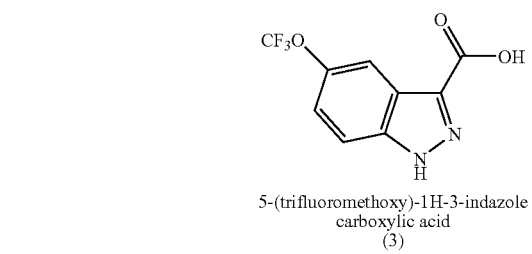

5-(trifluoromethoxy)-1H-3-indazole carboxylic acid (3)

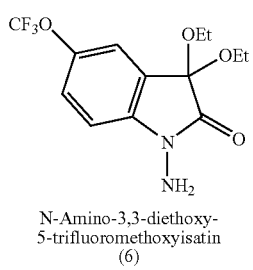

N-Amino-3,3-diethoxy-5-trifluoromethoxyisatin (6)

As mentioned above, compounds of the present invention can be used for the preparation of compounds of formula (I) in accordance with the procedures described in WO 2005/063767, WO 2005/092890, WO 2005/111038, WO 2006/001894 and WO 2006/069097. In particular, bicyclobase amides of formula (I) can be prepared from carboxylic acids, such as compound (3), and bicycloamines of formula $R^1$—H using standard peptide coupling agents, such as HBTU (O-benzotriazole-N,N,N',N'-tetramethyl-uronium-hexafluoro-phosphate), HATU (2-(1H-7-Azabenzotriazol-1-yl)-1,1,3,3-tetramethyl uronium hexafluorophosphate methanaminium), or HOBt (N-Hydroxybenzotriazole) and EDCI (1-[3-(dimethylamino)propyl]-3-ethylcarbodiimide hydrochloride), or by converting the acids to the corresponding acid chloride followed by reaction with the bicycloamine (Macor, J. E.; Gurley, D.; Lanthorn, T.; Loch, J.; Mack, R. A.; Mullen, G.; Tran, O.; Wright, N.; and J. E. Macor et al., "The 5-HT3-Antagonwast Tropisetron (ICS 205-930) was a Potent and Selective α-7 Nicotinic Receptor Partial Agonist," *Bioorg. Med. Chem. Lett.* 2001, 9, 319-321). The couplings are generally performed at room temperatures for 18-24 hours. The resultant adducts are then isolated and purified by standard techniques, such as chromatography or recrystallization, practiced by those skilled in the art.

The compounds of the present invention can be prepared according to the examples set out below. The examples are presented for purposes of demonstrating, but not limiting, the preparation of the compounds and compositions of this invention.

EXAMPLES

Example 1

Ketalization of 5-Trifluoromethoxyisatin (4) with Ethanol (Step 1)

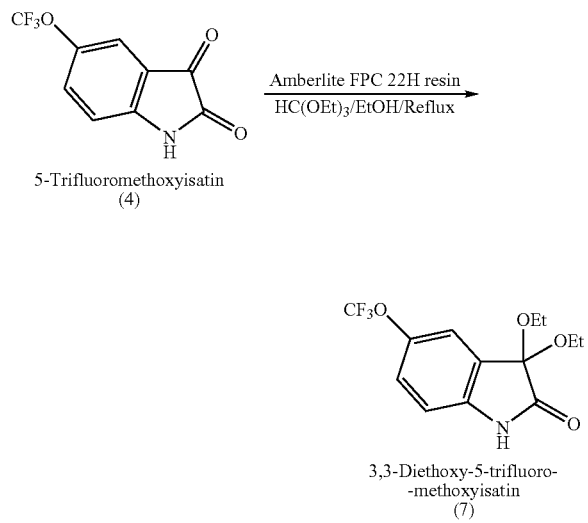

5-Trifluoromethoxyisatin
(4)

3,3-Diethoxy-5-trifluoro-methoxyisatin
(7)

A 1 L, four-necked, jacketed flask equipped with a thermocouple, nitrogen inlet/bubbler, condenser and a mechanical stirrer was charged with 50.0 g of 5-trifluoromethoxyisatin (4) (commercially available from, for example, Aldrich), and 25 g of Amberlite® FPC22H resin. The resin was distilled over toluene (200 ml/100 g) three times and dried at 40° C. under vacuum overnight. A quantity of 43 ml of HC(OEt)₃ and 400 ml of absolute ethanol was used. The reaction mixture was heated to reflux. The batch temperature was 76.5° C. and the jacket was set at 90° C. The mixture was held at reflux and a quantity of 21.5 ml of HC(OEt)₃ was charged at 90 minute, 180 minute, and 300 minute intervals. The mixture was held for another 2 hrs and the batch was cooled to 20° C. and filtered through a celite bed. The solution was collected and distilled to dryness under vacuum. The crude residue was re-slurried in 80 ml of 1:10 EtOAc/heptane and stirred at 0° C. for an hour and filtered to collect the product. Intermediate (7) was obtained in 80% yield and >99% HPLC purity.

Example 2

Amination of 3,3-Diethoxy-5-trifluoromethoxyisatin (7) with O-Benzoylhydroxylamine (Step 2)

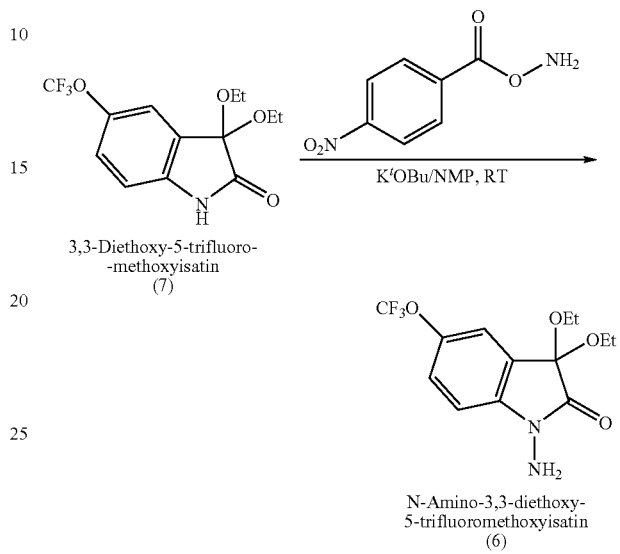

3,3-Diethoxy-5-trifluoro-methoxyisatin
(7)

N-Amino-3,3-diethoxy-5-trifluoromethoxyisatin
(6)

A 1 L, four-necked, jacketed flask equipped with a thermocouple, nitrogen inlet/bubbler, condenser and a mechanical stirrer was charged with 52.8 g of 3,3-diethoxy-5-trifluoromethoxyisatin (7) and 300 ml of anhydrous N-methylpyrrolidone (NMP). The mixture was stirred to form a clear light brown solution. A quantity of 227.0 ml of 1M potassium tert-butoxide solution in THF was charged drop wise at <25° C. and the mixture held an hour at that temperature after addition was complete. A quantity of 44.4 g of 4-nitrobenzoyl O-hydroxylamine was then charged as a solution in 100 ml of NMP and the mixture was stirred for 2 hours after addition was complete. The reaction was quenched with 300 ml of water at a temperature <25° C. The aqueous layer was extracted with 2×150 ml EtOAc and the combined organic layer was washed with 100 ml NaHCO₃ solution, then 3×200 ml of water and 200 ml of brine. The organic solution was concentrated to dryness and used in Example 3 without further purification.

Example 3

Ring opening, Deprotection, and Recyclization of N-Amino-3,3-diethoxy-5-trifluoromethoxyisatin (6) (Step 3)

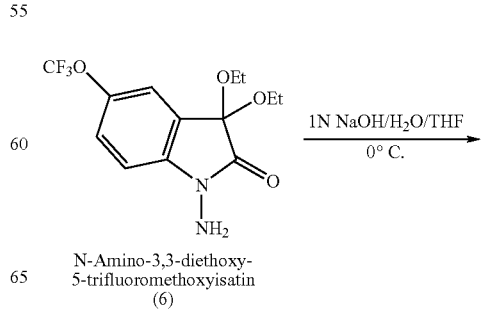

N-Amino-3,3-diethoxy-5-trifluoromethoxyisatin
(6)

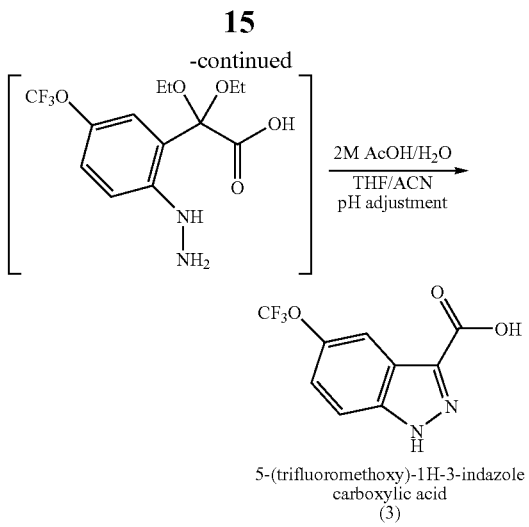

5-(trifluoromethoxy)-1H-3-indazole
carboxylic acid
(3)

A 1 L, four-necked, jacketed flask equipped with a thermocouple, nitrogen inlet/bubbler, condenser and a mechanical stirrer was charged with crude N-amino-3,3-diethoxy-5-trifluoromethoxyisatin (6) from Example 2 and 300 ml of THF. The mixture was stirred to form a solution and then cooled to 0° C. A quantity of 300 ml of 1N NaOH solution was slowly charged at a temperature <5° C. The mixture was stirred for 2 hrs at 0° C. A quantity of 300 ml of acetonitrile was slowly charged into the batch and the reaction was quenched at 0° C. with 2.0 M acetic acid solution in water drop wise at a temperature <5° C. until the final pH of the reaction reached 4. The reaction was warmed to room temperature after addition was complete and held overnight. The organic solvents were distilled at room temperature and the reaction mixture was extracted with 300×150 ml of EtOAc. The combined organic layers were washed with 3×100 ml of water and then 100 ml of brine. The organic layer was concentrated to dryness and re-slurried in 1:10 EtOAc/heptane, stirred for 1 hour, and then filtered to collect the final product. The overall yield was 70% with a 98.5% HPLC purity based on compound (4).

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

General Procedure A

Method for Coupling 3-aminoquinuclidine and carboxylic acids to Form the Corresponding carboxamides To a solution of the carboxylic acid (16.1 mmol) in N,N-dimethylformamide (65 mL) was added HBTU (16.1 mmol) or HATU (16.1 mmol), catalytic amount of dimethylaminopyridine, N,N-diisopropylethylamine (96.6 mmol) and 4 Å activated molecular sieves (2.6 g). The reaction mixture was maintained at room temperature for 2 h under nitrogen and then 3-aminoquinuclidine dihydrochloride (16.1 mmol) was added. After 18 h, the solvent was removed under reduced pressure. The oily residue was partitioned between saturated, aqueous sodium bicarbonate (25 mL) and dichloromethane (100 mL). The aqueous layer was further extracted with 9/1 dichloromethane/methanol (5×100 mL) and the combined organic layers were concentrated. The residue was purified by chromatography [90/10/1 dichloromethane/methanol/ammonium hydroxide or 1/1 to 0/1 ethyl acetate/(70/30/1 ethyl acetate/methanol/ammonium hydroxide)] or by preparative HPLC, thus providing the product in 30%-70% yield.

The free base was dissolved in methanol (3.5 mL/mmol starting acid) and treated with 1N hydrochloric acid in ether (3.5 mL/mmol starting acid). The resulting suspension was diluted with ether (7 mL/mmol starting acid) and was maintained at room temperature for 2 h. The solids were collected by filtration, rinsed with ether, and dried, thus providing the hydrochloride salt in 40-60% yield.

Example 4

N-[(3S)-1-Azabicyclo[2.2.2]oct-3-yl]-5-(trifluoromethoxy)-1H-indazole-3-carboxamide hydrochloride

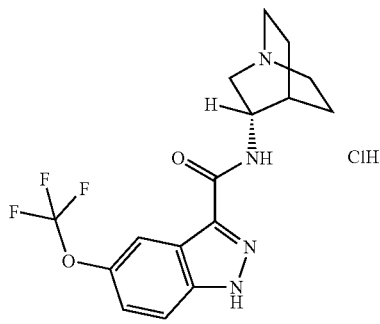

The title compound was prepared using general Procedure A in 60% yield.

LC/MS (EI) $t_R$ 5.13, m/z 355 (M$^+$+1).

We claim:
1. A method for preparing compound (3) having the formula:

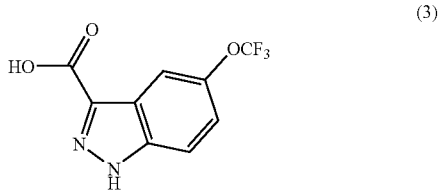

which comprises:
(a) reacting 5-trifluoromethoxyisatin with a ketone-protecting reagent in a solvent to provide a ketone-protected compound;
(b) treating the ketone-protected compound from step (a) with an electrophilic aminating reagent in an inert solvent to provide an electrophilically aminated compound; and
(c) hydrolyzing the electrophilically aminated compound from step (b) under basic conditions to form a ring opened intermediate and treating the intermediate with aqueous acid to ring close the intermediate and remove the ketone-protecting reagent to provide (3).

2. The method according to claim 1, wherein the ketone-protecting reagent in step (a) is HC(OEt)$_3$/EtOH.

3. The method according to claim 1, wherein the ketone-protected compound in step (a) is 3,3-diethoxy-5-trifluoromethoxyisatin.

4. The method according to claim 1, wherein the ketone-protected compound in step (a) is prepared by heating to reflux a mixture of 5-trifluoromethoxyisatin, an acid cation exchange resin, $HC(OEt)_3$, and absolute ethanol.

5. The method according to claim 1, wherein the electrophilic aminating reagent in step (b) is 4-nitrobenzoyl O-hydroxylamine.

6. The method according to claim 1, wherein the electrophilically aminated compound in step (b) is N-amino-3,3-diethoxy-5-trifluoromethoxyisatin.

7. The method according to claim 1, wherein the electrophilically aminated compound in step (b) is prepared by sequentially admixing 3,3-diethoxy-5-trifluoromethoxyisatin and N-methylpyrrolidone, adding to the mixture potassium tert-butoxide solution in tetrahydrofuran at <25° C., and then adding to the mixture 4-nitrobenzoyl O-hydroxylamine in N-methylpyrrolidone.

8. The method according to claim 1, wherein the hydrolysis under basic conditions from step (c) is carried with aqueous sodium hydroxide.

9. The method according to claim 1, wherein the treatment of the intermediate with aqueous acid from step (c) is carried with aqueous acetic acid at <5° C.

* * * * *